US008383861B2

(12) United States Patent
Do et al.

(10) Patent No.: US 8,383,861 B2
(45) Date of Patent: Feb. 26, 2013

(54) METHODS FOR MAKING ETHANOLAMINE(S) AND ETHYLENEAMINE(S) FROM ETHYLENE OXIDE AND AMMONIA, AND RELATED METHODS

(75) Inventors: David Do, Brentwood, CA (US); Christopher H. Domke, Rosharon, TX (US); Jacinto Lopez-Toledo, Lake Jackson, TX (US); David M. Petraitis, Covington, LA (US); Thomas Z. Srnak, Arlington Heights, IL (US)

(73) Assignee: Dow Global Technologies LLC, Midland, MI (US)

( * ) Notice: Subject to any disclaimer, the term of this patent is extended or adjusted under 35 U.S.C. 154(b) by 448 days.

(21) Appl. No.: 12/587,358

(22) Filed: Oct. 6, 2009

(65) Prior Publication Data

US 2010/0087684 A1 Apr. 8, 2010

Related U.S. Application Data

(60) Provisional application No. 61/195,405, filed on Oct. 6, 2008.

(51) Int. Cl.
C07C 209/00 (2006.01)
(52) U.S. Cl. ......................................... 564/478; 564/497
(58) Field of Classification Search .................. None
See application file for complete search history.

(56) References Cited

U.S. PATENT DOCUMENTS

| | | | |
|---|---|---|---|
| 2,861,995 A | 11/1958 | MacKenzie | |
| 3,110,732 A | 11/1963 | Speranza et al. | |
| 3,394,186 A | 7/1968 | Muhlbauer | |
| 3,658,692 A | 4/1972 | Gilbert et al. | |
| 3,847,754 A | 11/1974 | Oliver | |
| 4,032,411 A | 6/1977 | Tornquist et al. | |
| 4,073,750 A | 2/1978 | Yates et al. | |
| 4,111,840 A | 9/1978 | Best | |
| 4,123,462 A | 10/1978 | Best | |
| 4,209,424 A | 6/1980 | Le Goff et al. | |
| 4,264,776 A | 4/1981 | Hershman et al. | |
| 4,328,370 A | 5/1982 | Fazio | |
| 4,400,539 A | 8/1983 | Gibson et al. | |
| 4,404,405 A * | 9/1983 | Winters | 564/482 |
| 4,510,263 A | 4/1985 | Pereira et al. | |
| 4,552,961 A | 11/1985 | Herdle | |
| 4,568,746 A | 2/1986 | Cowherd, III | |
| 4,584,405 A | 4/1986 | Vanderpool | |
| 4,602,091 A | 7/1986 | Brennan | |
| 4,708,945 A | 11/1987 | Murrell et al. | |
| 4,729,981 A | 3/1988 | Kobylinski et al. | |
| 4,801,573 A | 1/1989 | Eri et al. | |
| 4,806,517 A | 2/1989 | Vanderpool et al. | |
| 4,845,296 A * | 7/1989 | Ahmed et al. | 564/477 |
| 4,870,044 A | 9/1989 | Kukes et al. | |
| 4,883,826 A | 11/1989 | Marugg et al. | |
| 4,888,316 A | 12/1989 | Gardner et al. | |
| 4,906,782 A | 3/1990 | Hara et al. | |
| 4,922,024 A | 5/1990 | Bowman et al. | |
| 4,927,931 A | 5/1990 | Molzahn et al. | |
| 4,983,735 A | 1/1991 | Hartwell et al. | |
| 5,030,740 A | 7/1991 | Bowman et al. | |
| 5,073,635 A | 12/1991 | Bowman et al. | |
| 5,120,815 A | 6/1992 | Marugg et al. | |
| 5,166,442 A | 11/1992 | Hartwell et al. | |
| 5,225,599 A | 7/1993 | King et al. | |
| 5,225,600 A | 7/1993 | King et al. | |
| 5,248,827 A | 9/1993 | Hara et al. | |
| 5,256,786 A | 10/1993 | Bowman et al. | |
| 5,288,909 A | 2/1994 | Hartwell et al. | |
| 5,321,160 A | 6/1994 | Hironaka et al. | |
| 5,352,835 A | 10/1994 | Dai et al. | |
| 5,410,087 A | 4/1995 | Hartwell et al. | |
| H1447 H | 6/1995 | Linton | |
| 5,455,352 A | 10/1995 | Huellmann et al. | |
| 5,552,363 A | 9/1996 | Pannell et al. | |
| 5,554,793 A | 9/1996 | Hartwell et al. | |
| 5,721,305 A | 2/1998 | Eshuis et al. | |
| 5,750,790 A | 5/1998 | King | |
| 5,851,948 A | 12/1998 | Chuang et al. | |
| 5,935,889 A | 8/1999 | Murrell et al. | |
| 6,117,814 A | 9/2000 | Plecha et al. | |
| 6,124,367 A | 9/2000 | Plecha et al. | |
| 6,169,207 B1 | 1/2001 | Tsuneki et al. | |
| 6,222,008 B1 | 4/2001 | Gelles | |
| 6,235,677 B1 | 5/2001 | Manzer et al. | |
| 6,306,795 B1 | 10/2001 | Ryan et al. | |

(Continued)

FOREIGN PATENT DOCUMENTS

| | | |
|---|---|---|
| EP | 0075940 | 4/1983 |
| EP | 0163253 | 12/1985 |

(Continued)

OTHER PUBLICATIONS

Komiyama et al., "Concentration Profiles in Impregnation of Porous Catalysts: Nickel on Alumina," Journal of Catalysis, vol. 63, School of Chemical Engineering, Cornell University, and Chevron Research Company, pp. 35-52 (1980).
Database Beilstein [Online] Beilstein Institute for Organic Chemistry, Frankfurt-Main, DE; 1951, XP002576591, Database accession No. 845679 (reaction ID) abstract & Jur'ew, Lewi: Doklady Akademii Nauk SSSR, vol. 78, 1951, pp. 725-727, ISSN: 0002-3264.
Reichle, "Reactions of Aliphatic α-ω- Diamines in H+-Pentasils," Journal of Catalysis, vol. 144, Union Carbide Chemicals and Plastics Company, Inc., Specialty Chemicals Division, pp. 556-568 (1993).
Tanabe et al., "A New Hypothesis Regarding the Surface Acidity of Binary Metal Oxides," Bulletin of the Chemical Society of Japan, vol. 47(5), Department of Chemistry, Faculty of Science, Hokkaido University, pp. 1064-1066 (1974).

(Continued)

Primary Examiner — Johann Richter
Assistant Examiner — James Meadows
(74) Attorney, Agent, or Firm — Kagan Binder, PLLC

(57) ABSTRACT

The present invention relates to processes for the manufacture of one or more ethanolamines and one or more ethyleneamines starting from the reaction of ethylene oxide with ammonia to produce one or more ethanolamines and the conversion of the ethanolamine(s) to ethyleneamine(s). The present invention also relates to separating alkylethyleneamines from ethyleneamines.

19 Claims, 4 Drawing Sheets

U.S. PATENT DOCUMENTS

| | | | |
|---|---|---|---|
| 6,465,530 B2 | 10/2002 | Roy-Auberger et al. |
| 6,469,214 B2 | 10/2002 | Melder et al. |
| 6,534,441 B1 | 3/2003 | Bartley et al. |
| 6,576,796 B1 | 6/2003 | Funke et al. |
| 6,703,343 B2 | 3/2004 | Park |
| 6,977,273 B2 | 12/2005 | Roy-Auberger et al. |
| 7,045,485 B2 | 5/2006 | Kelkar et al. |
| 7,053,246 B2 | 5/2006 | Gerlach et al. |
| 7,053,247 B2 | 5/2006 | Lif et al. |
| 7,056,857 B2 | 6/2006 | Srinivasan et al. |
| 7,067,455 B2 | 6/2006 | Chen et al. |
| 7,256,154 B2 | 8/2007 | Moon et al. |
| 7,323,100 B2 | 1/2008 | Espinoza et al. |
| 7,341,976 B2 | 3/2008 | Espinoza et al. |
| 7,348,293 B2 | 3/2008 | Timken |
| 7,393,978 B2 | 7/2008 | Frauenkron et al. |
| 7,541,310 B2 | 6/2009 | Espinoza et al. |
| 7,595,276 B2 | 9/2009 | Kodama et al. |
| 7,745,369 B2 | 6/2010 | Bhan et al. |
| 7,769,619 B1 | 8/2010 | Krysinski et al. |
| 7,824,656 B2 | 11/2010 | Idem et al. |
| 7,981,836 B2 | 7/2011 | Kanazirev et al. |
| 2003/0013873 A1 | 1/2003 | Neumann et al. |
| 2005/0095189 A1 | 5/2005 | Brey et al. |
| 2006/0030726 A1 | 2/2006 | Telschow |
| 2007/0100144 A1 | 5/2007 | Frauenkron et al. |
| 2008/0003131 A1 | 1/2008 | Bauer et al. |
| 2010/0056366 A1 | 3/2010 | Lee |
| 2010/0087681 A1 | 4/2010 | Petraitis et al. |
| 2010/0087682 A1 | 4/2010 | King et al. |
| 2010/0087683 A1 | 4/2010 | Cook et al. |
| 2010/0087685 A1 | 4/2010 | King et al. |
| 2010/0094007 A1 | 4/2010 | King et al. |
| 2010/0094008 A1 | 4/2010 | King et al. |
| 2010/0137642 A1 | 6/2010 | King et al. |

FOREIGN PATENT DOCUMENTS

| | | |
|---|---|---|
| EP | 0197611 | 10/1986 |
| EP | 0197612 | 10/1986 |
| EP | 0254335 | 1/1988 |
| EP | 0284398 | 9/1988 |
| EP | 0526851 | 2/1993 |
| EP | 0737669 | 10/1996 |
| EP | 1211238 | 6/2002 |
| EP | 1249440 | 10/2002 |
| GB | 1508460 | 4/1978 |
| IL | 57019 | 9/1983 |
| JP | 05 09777 | 4/1993 |
| RU | 2186761 | 8/2002 |
| RU | 2226188 | 3/2004 |
| RU | 2226189 | 3/2004 |
| WO | WO 99/24389 | 5/1999 |
| WO | WO 01/44150 | 6/2001 |
| WO | WO 01/66247 | 9/2001 |
| WO | WO 01/98243 | 12/2001 |
| WO | WO 03/010125 | 2/2003 |
| WO | WO 2005/012223 | 2/2005 |
| WO | WO 2005/014523 | 2/2005 |
| WO | WO 2005/061430 | 7/2005 |
| WO | WO 2006/053342 | 5/2006 |
| WO | WO 2006/060206 | 6/2006 |
| WO | WO 2006/114417 | 11/2006 |
| WO | WO 2007/093514 | 8/2007 |
| WO | WO 2008/104582 | 9/2008 |
| WO | WO 2009/083580 | 7/2009 |

OTHER PUBLICATIONS

"Simultaneous manufacture of acyclic and cyclic di- and polyethylenepolyamines," Zagidullun, R.N., USSR., Khimicheskaya Promyshlennost (Moscow, Russian Federation) (1987), (5), 267-9. CODEN: KPRMAW ISSN: 0023-110X. Journal written in Russian. CAN 107:58453, AN 1987: 458453 CAPLUS.

Database CAPLUS [Online] Chemical Abstracts Service, Columbus, Ohio, US; 2005, Kiebach, Ragnar et al.: "Solvothermal synthesis of (C6H17N3) Sb10S16: A new thioantimonate(III) with an in-situ formed organic amine cation," XP002562885 retrieved from STN Database accession No. 2005: 168744 Abstract & Zeitschrift für Naturforschung, B: 2004, 59 (Nov. 2012),1314-1319.

Fluid Phase Equilibria, Olson, James D., Thermodynamics of hydrogen-bonding mixtures 4: $G^E$, $H^E$, $S^E$ and $C^E_p$ and possible double azeotropy of water + $N$-methylethylenediamine, vol. 185, p. 209-218, (2001).

\* cited by examiner

METHODS FOR MAKING ETHANOLAMINE(S) AND ETHYLENEAMINE(S) FROM ETHYLENE OXIDE AND AMMONIA, AND RELATED METHODS

PRIORITY CLAIM

The present non-provisional patent Application claims priority under 35 U.S.C. §119(e) from U.S. Provisional patent application having Ser. No. 61/195,405 filed on Oct. 6, 2008, by Do et al. and entitled "METHODS FOR MAKING ETHANOLAMINE(S) AND ETHYLENEAMINE(S) FROM ETHYLENE OXIDE AND AMMONIA, AND RELATED METHODS," which application is incorporated herein by reference in its entirety.

FIELD OF THE INVENTION

The present invention relates to processes for the manufacture of one or more ethanolamines and one or more ethyleneamines starting from the reaction of ethylene oxide with ammonia to produce one or more ethanolamines and the subsequent conversion of the ethanolamine(s) to ethyleneamine(s). The present invention also relates to separating alkylethyleneamines from ethyleneamine.

BACKGROUND OF THE INVENTION

Multi-reaction processes for making product mixtures of ethanolamines and ethyleneamines from ethylene oxide and ammonia are known. See, for example, PCT Publication Number WO 2006/114417 and U.S. Pat. No. 4,400,539 (Gibson et al.).

PCT Publication Number WO 2006/114417 discloses a method for producing ethyleneamines, in which ethylene oxide (EO) is continuously reacted with ammonia on an inorganic ion exchanger as a heterogeneous catalyst in anhydrous conditions in a first reaction stage, the obtained reaction product containing monoethanolamine (MEOA), diethanolamine (DEOA), and triethanolamine (TEOA) at a weight ratio MEOA:DEOA:TEOA=80-94:5.9-15:0.1-5, and the reaction product is then continuously reacted with ammonia in the presence of hydrogen and a heterogeneous hydrogenation catalyst in a second reaction stage.

Gibson et al. discloses a continuous process for the manufacture of ethylenediamine from the products of the reaction of ethylene oxide and ammonia, provision of a continuous recycle stream of monoethanolamine to the products of the reaction of ethylene oxide and ammonia, the amination of such products of the reaction of ethylene oxide and ammonia combined with the monoethanolamine recycle in which the feed stream to the amination reaction zone contains at least 70 weight percent monoethanolamine as well as diethanolamine and triethanolamine, the moles of ammonia provided to the amination reaction exceeds the molar concentration of alcoholic hydroxyl groups present in the amination feed, and the feed to the amination reactor contains at least a 5% increase in the concentration of monoethanolamine over the concentration of monoethanolamine in the reaction product stream from the reaction of ethylene oxide and ammonia.

There is an ongoing desire to improve upon such known processes by reducing capital costs, reducing energy costs/improving operating efficiency, improving catalyst selectivity, improving product quality, improving product selectivity, combinations of these, and the like.

For example, it is desirable to manufacture ethanolamines and ethyleneamines from ethylene oxide and ammonia with the minimum amount of unit operations (e.g., ammonia recycle systems, water removal systems, combinations of these, and the like), yet be able to keep impurity levels at a minimum by reducing the production of impurities as by-products and/or being able to remove by-product impurities more effectively.

SUMMARY OF THE INVENTION

Alkylamines can be generated in the reductive amination of ethanolamines and ammonia to form ethyleneamines. Such alkylamines are generally considered impurities. In addition, if ammonia is separated from the effluent of the reductive amination reaction at least a portion of the alkylamines tend to be in admixture with the separated ammonia. If the admixture of ammonia and alkylamines is recycled to the reaction of ethylene oxide and ammonia, the alkylamines can unfortunately become ethoxylated and create new species of impurities (alkylethanolamines), which can impact one or more of product quality, product selectivity, and process performance, to an undue degree. Further, these alkylethanolamines can produce alkylethyleneamines when subjected to a reductive amination process. Alkylethyleneamines can be challenging to separate from parent amines. For example, in some applications, ethylenediamine product can tolerate a certain level of the alkylethylenediamines. In other applications, the alkylethylenediamine content of ethylenediamine product is specified to be relatively quite low.

The present invention can recycle unreacted ammonia to the process for making ethanolamines and ethyleneamines in a manner such that alkylamine impurities generated by reductive amination of ethanolamines and ammonia to ethyleneamines and that are in admixture with the ammonia, are separated from the ammonia before the ammonia is recycled to the process (e.g., before the ammonia is recycled to the reaction of ethylene oxide and ammonia). The present invention can also recycle unreacted ammonia to the process for making ethanolamines and ethyleneamines in a manner such that alkylamine impurities generated by reductive amination of ethanolamines and ammonia to ethyleneamines and that are in admixture with the ammonia, are recycled to the reductive amination reaction, but not the reaction of ethylene oxide and ammonia.

Advantageously, by handling the alkylamine impurities according to the present invention, ammonia can be recycled to one or more points in the overall process, yet the presence of an undue amount of the alkylamines in the reaction of ethylene oxide and ammonia is avoided. Also, by handling the alkylamine impurities according to the present invention, the reaction of ethylene oxide and ammonia and the reductive amination reaction can be integrated in a manner that minimizes the overall number of unit operations such as ammonia recycle, water removal, product refining, combinations of these, and the like. For example, the ethanolamine and ethyleneamine production operations can be directly coupled so that a single plant or train can be used for their production. Such a process can reduce the overall footprint of equipment and, therefore, reduce capital investment and operating cost.

The present invention can also take advantage of an azeotrope that can be formed between water and alkylethylenediamines such that the alkylethylenediamines can be separated from ethylenediamine to a satisfactory level.

Advantageously, such an azeotropic removal of alkylethylenediamines can permit removal of alkylethylenediamines at relatively moderate conditions, thereby saving energy costs.

It has also been discovered that if one or more ethanolamines are reacted with ammonia in the presence of an improved reductive amination catalyst under improved operating conditions, improved ethylenediamine selectivity can be realized. Adding additional monoethanolamine to that already produced via ethylene oxide and ammonia can be done if desired but is not necessary.

According to one aspect of the present invention, a process for the manufacture of one or more ethanolamines and one or more ethyleneamines includes the steps of: a) combining ethylene oxide with ammonia; b) a first reacting step including reacting ethylene oxide with ammonia in a manner to produce one or more ethanolamines, wherein said first reacting step forms a first effluent including: i) unreacted ammonia; and ii) the one or more ethanolamines; c) a second reacting step including reacting at least a portion of the first effluent in the presence of a reductive amination catalyst to produce one or more ethyleneamines, wherein said second reacting step forms a second effluent including: i) unreacted ammonia; ii) one or more alkylamines; iii) one or more unreacted ethanolamines; and iv) the one or more ethyleneamines; d) separating the unreacted ammonia and one or more alkylamines from the second effluent; e) separating the unreacted ammonia from the one or more alkylamines; and f) after separating the unreacted ammonia from the one or more alkylamines, recycling the unreacted ammonia so as to be combined with the ethylene oxide in the step of combining ethylene oxide with ammonia.

According to another aspect of the present invention, a process for the manufacture of one or more ethanolamines and one or more ethyleneamines includes the steps of: a) combining ethylene oxide with ammonia; b) a first reacting step including reacting ethylene oxide with ammonia in a manner to produce one or more ethanolamines, wherein said first reacting step forms a first effluent including: i) unreacted ammonia; and ii) the one or more ethanolamines; c) separating at least a portion of the unreacted ammonia from the first effluent; d) after separating the at least a portion of the unreacted ammonia from the first effluent, recycling the unreacted ammonia so as to be combined with the ethylene oxide in the step of combining ethylene oxide with ammonia; e) a second reacting step including reacting one or more ethanolamines made in the first reacting step and ammonia in the presence of a reductive amination catalyst to produce one or more ethyleneamines, wherein said second reacting step forms a second effluent including: i) unreacted ammonia; ii) one or more alkylamines; iii) one or more unreacted ethanolamines; and iv) the one or more ethyleneamines; f) separating at least a portion of the unreacted ammonia and at least a portion of the one or more alkylamines from the second effluent; and g) after separating the unreacted ammonia and at least a portion of the one or more alkylamines from the second effluent, recycling the unreacted ammonia and the at least a portion of the one or more alkylamines so as to be combined with the one or more ethanolamines and ammonia in the second reacting step.

According to another aspect of the present invention, a process for the manufacture of one or more ethanolamines and one or more ethyleneamines includes the steps of: a) combining ethylene oxide with ammonia; b) a first reacting step including reacting ethylene oxide with ammonia in a manner to produce one or more ethanolamines, wherein said first reacting step forms a first effluent including: i) unreacted ammonia; and ii) the one or more ethanolamines; c) separating at least a portion of the unreacted ammonia from the first effluent so as to form a second effluent; d) after separating the at least a portion of the unreacted ammonia from the first effluent, recycling the unreacted ammonia so as to be combined with the ethylene oxide in the step of combining ethylene oxide with ammonia; e) a second reacting step including reacting at least a portion of the second effluent in the presence of a reductive amination catalyst to produce one or more ethyleneamines, wherein said second reacting step forms a third effluent including: i) unreacted ammonia; ii) one or more alkylamines; iii) one or more unreacted ethanolamines; and iv) the one or more ethyleneamines f) separating the unreacted ammonia and at least a portion of the one or more alkylamines from the third effluent; g) after separating the unreacted ammonia and at least a portion of the one or more alkylamines from the third effluent, recycling the unreacted ammonia and the at least a portion of the one or more alkylamines so as to be combined with the second effluent.

According to another aspect of the present invention, a process for the manufacture of one or more ethanolamines and one or more ethyleneamines includes the steps of: a) combining ethylene oxide with ammonia; b) a first reacting step including reacting ethylene oxide with ammonia in a manner to produce one or more ethanolamines including at least monoethanolamine, wherein unreacted ammonia is left over after said reacting step; c) forming a first reactant stream consisting essentially of the monoethanolamine and unreacted ammonia from the first reacting step; and d) a second reacting step including reacting the first reactant stream in the presence of a reductive amination catalyst to produce one or more ethyleneamines.

According to another aspect of the present invention, a process for separating one or more alkylethylenediamines from ethylenediamine includes the steps of: a) providing a composition including: i) ethylenediamine; ii) water; and iii) one or more alkylethylenediamines; b) causing the composition to be subjected to conditions such that an azeotrope forms between the water and the one or more alkylethylenediamines; and c) separating the one or more alkylethylenediamines and at least a portion of the azeotropic water from the composition.

According to another aspect of the present invention, a process for the manufacture of one or more ethyleneamines includes the steps of a) reacting monoethanolamine with ammonia in the presence of a reductive amination catalyst to produce one or more ethyleneamines, wherein said reaction also produces water and one or more alkylethyleneamines as by-products, and wherein said reacting step forms an effluent including: i) the one or more ethyleneamines; ii) the water; and iii) the one or more alkylethyleneamines; b) causing the effluent to be subjected to conditions such that an azeotrope forms between the water and the one or more alkylethyleneamines; and c) separating the one or more alkylethyleneamines and at least a portion of the azeotropic water from the effluent.

According to another aspect of the present invention, a process for the manufacture of ethylenediamine includes the steps of: a) reacting monoethanolamine with ammonia in the presence of a reductive amination catalyst to produce at least ethylenediamine, wherein said reaction produces water and one or more alkylethylenediamines as by-products, wherein said reacting step forms an effluent including: i) the ethylenediamine; ii) the water; and iii) the one or more alkylethylenediamines; b) causing the effluent to be subjected to conditions such that an azeotrope forms between the water and the one or more alkylethylenediamines; c) separating the one or more alkylethylenediamines and at least a portion of the azeotropic water from the effluent.

BRIEF DESCRIPTION OF THE DRAWINGS

The advantages of the present invention, and the manner of attaining them, will become more apparent and the invention itself will be better understood by reference to the following description of the embodiments of the invention taken in conjunction with the accompanying drawing, wherein.

DETAILED DESCRIPTION

Figure 1:
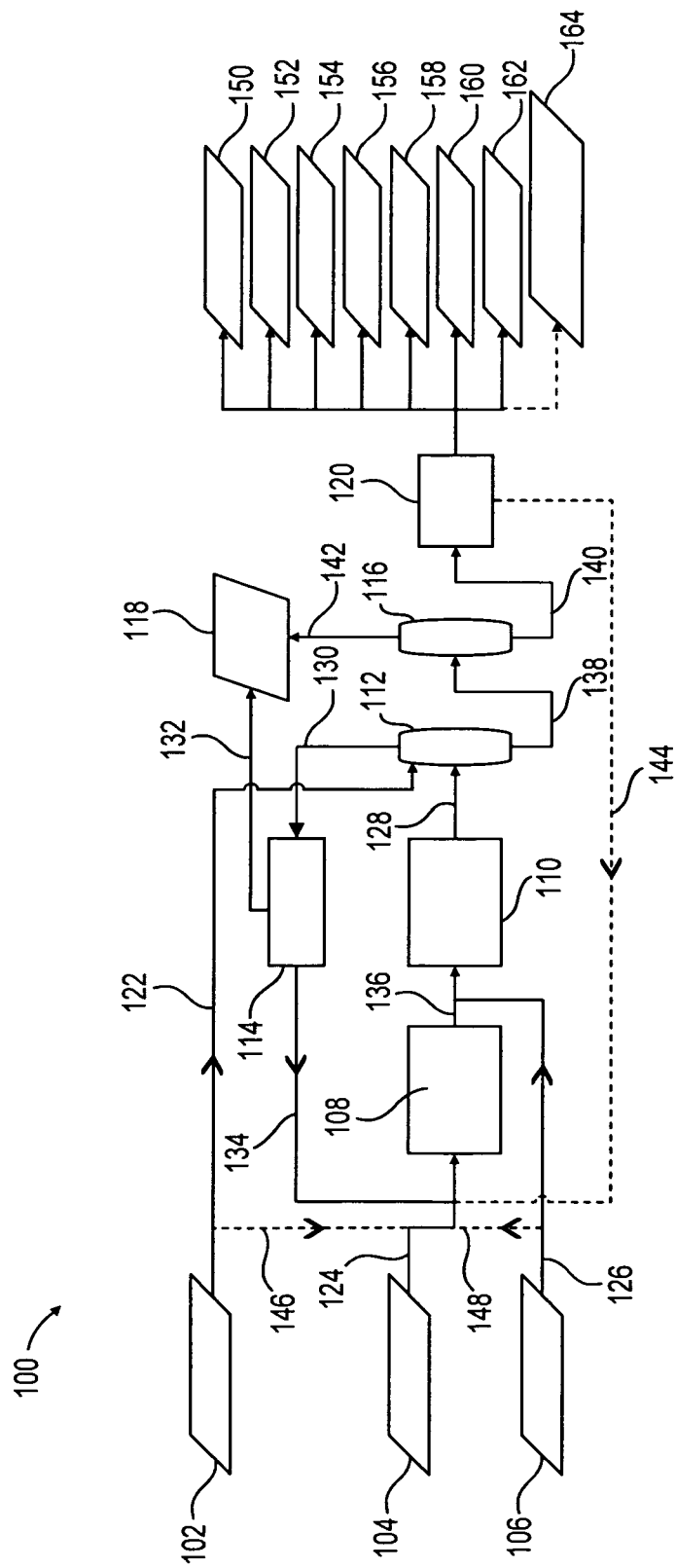
FIG. 1 shows a schematic flow diagram of one embodiment for preparing ethanolamines and ethyleneamines from ethylene oxide and ammonia according to the present invention.

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention. While the present invention will be described in the specific context of using ethylene oxide and ammonia for the manufacture of one or more ethanolamines and one or more ethyleneamines, the principles of the invention may be applicable to other chemical manufacturing processes that can share one or more components of an effluent stream from one process with one or more other processes as well.

All publications and patents mentioned herein are incorporated herein by reference in their respective entireties for the purpose of describing and disclosing, for example, the constructs and methodologies that are described in the publications which might be used in connection with the presently described invention. The publications discussed above and throughout the text are provided solely for their disclosure prior to the filing date of the present application. Nothing herein is to be construed as an admission that the inventor is not entitled to antedate such disclosure by virtue of prior invention.

One or more ethanolamines can be manufactured by reacting ethylene oxide with ammonia. Ethanolamines are well known in the art and include monoethanolamine (also referred to as ETA, MEA, or MEOA), diethanolamine (also referred to as DEA or DEOA), and triethanolamine (also referred to as TEA or TEOA).

The process which may be employed to provide a product stream of ethanolamines by the reaction of ethylene oxide and ammonia may be any one of the processes described in the prior art which involve the reaction of ethylene oxide with ammonia to produce a mixture of monoethanolamine, diethanolamine and triethanolamine. Illustrative of such processes are those described in U.S. Pat. No. 4,400,539 (Gibson et al.) and PCT Publication Number WO 2006/114417.

With respect to making ethanolamines, it is preferred that a large excess of ammonia relative to the ethylene oxide be used in the reaction so as to obtain yields of monoethanolamine of at least 65 weight percent, preferably at least 70 weight percent. In a typical practice of the invention in order to obtain these desirable yields of monoethanolamine, one may employ between about 5 to about 50 moles, and preferably between about 15 to 30 moles, of ammonia for each mole of ethylene oxide.

The ammonia that is combined with the ethylene oxide can be freshly added ammonia, recycled ammonia, or combinations thereof. The fresh ammonia can be fed directly into a reactor or at some other point in the process (e.g., to an ammonia recovery unit). Ammonia suitable for the reaction between ethylene oxide and ammonia can be anhydrous or a solution of ammonia and water.

Optionally, the presence of a small amount of water in the reaction mixture of ethylene oxide and ammonia can have an advantageous catalytic effect on the reaction rate for forming ethanolamines. In preferred embodiments, the amount of water can be relatively small to effect this kind of result. In general from anhydrous to about 3% to about 5% by weight of water based on the weight of the reaction mixture may be utilized to catalytically induce the reaction. Though greater amounts of water may be desirable or useful to affect the aforementioned catalysis, such amounts need not be employed and indeed, in the preferable case, relatively large amounts of water are avoided to limit the energy requirements needed to separate water from the product mixture and are avoided due to undesirable reactions that may occur between ethylene oxide and the water.

Optionally, hydrogen gas can be introduced into the reaction mixture of ethylene oxide and ammonia to help improve color and/or reduce impurities with respect to the products of reaction.

The reaction between ethylene oxide and ammonia to produce ethanolamine(s) is catalytic. Depending on, e.g., product mix objectives, a heterogeneous or homogeneous catalyst can be used to catalyze the reaction. A homogeneously and auto-catalyzed reaction is where, e.g. temperature, water, and/or recycling of ethanolamines can catalyze the reaction. Significantly, a homogeneously catalyzed reaction between ethylene oxide and ammonia can relatively reduce impurities, which can beneficially impact (improve) product quality and yields.

The reaction between ethylene oxide and ammonia may be run batch-wise or continuously.

In the most preferred embodiment, it is desirable to effect the reaction in a plug-flow type reactor by feeding a stream including at least ammonia and ethylene oxide to one end of a tubular plug-flow type reactor and withdrawing the effluent containing the desired ethanolamines from the other end thereof. It can also be very desirable in the practice of the invention to maximize the plug-flow characteristics of the reactor and for this reason the geometry of the reactor is preferably such as to minimize any back mixing or internal recycling that might occur as a consequence of improper reactor design or improper fluid velocities. A turbulent single directional flow of the reaction mixture through a plug-flow type reactor, under plug-flow type reaction conditions, can desirably result in the flow of the stream through the reactor with a minimum amount of back mixing and thermal stratification. This tends to essentially eliminate hot spots in the reactor which can affect the reaction rates and product distribution to an undue degree, i.e., as between monoethanolamine, diethanolamine and triethanolamine, and minimize the reaction of ethylene oxide with already formed ethanolamines. In alternative embodiments, a series of reactors can be used which in combination achieve the results of a plug-flow type reaction system.

The reaction between ethylene oxide and ammonia to produce ethanolamine(s) can be performed in a tubular adiabatic reactor, an isothermal reactor, or a fixed bed reactor.

Optionally, one or more auxiliary unit operations can be used in combination with the reactor(s) for carrying out the reaction of ethylene oxide and ammonia. For example, the reaction effluent can be cooled if additional control on subsequent processes is desired (e.g., the reaction of one or more ethanolamines with ammonia as discussed below). Such cooling can be performed using equipment well known in the art, such as via a conventional cooler, an integrated process/process heat exchanger, combinations of these, and the like.

The process for making the ethanolamines involves reacting a fluid stream of a mixture of ethylene oxide and ammonia. The fluid stream can be a dense vapor, liquid, or supercritical. The stream is preferably maintained in a single, homogeneous, supercritical phase. This supercritical phase is preferably maintained for a period of time sufficient to permit the reaction to proceed to completion and thus to form a desired product mixture. The stream can be maintained in a single, homogeneous, supercritical phase by selecting a temperature and a pressure which creates such a phase. Alternatively, the reactants can be present in a two-phase fluid stream, a single phase vapor stream or a single phase liquid stream.

In practicing this preferred process for making the ethanolamines, the temperatures employed to carry out the reaction between ethylene oxide and ammonia are preferably above the critical temperature of the reaction mixture. When maintained at such a temperature, coupled with pressure (discussed below), a single supercritical phase can be achieved within which the reaction between ethylene oxide and ammonia can occur. The reaction can proceed when the reaction mixture is maintained above its critical temperature to achieve the single supercritical phase.

Accordingly, the temperature is preferably above the critical temperature for the reaction mixture in order to achieve the supercritical phase. Preferably, the temperature is in the range of from 130° C. to 225° C., although the upper limit of the reaction temperature may be higher as long as the critical temperature of the reaction mixture is exceeded. Even more preferred, the reaction temperature can be in the range of from 150° C. to 210° C., and even more preferably from 170° C. to 190° C.

The reaction between ethylene oxide and ammonia may be run under isothermal or adiabatic conditions. Under isothermal conditions, since the reaction is strongly exothermic, heat may be withdrawn from the reaction mixture to keep the temperature approximately constant. Preferably, the reaction between ethylene oxide and ammonia is carried out under adiabatic conditions. In cases where the reaction is to be carried out under adiabatic or nearly adiabatic conditions, the reactants are preferably preheated to a temperature which is at least sufficient to effect an interaction between the reactants, such as a temperature as low as 20° C. and higher.

Preferably, the reactant mixture is at a temperature and pressure sufficient to achieve and maintain a single phase or a supercritical phase so as to achieve a desired reaction rate The pressure of the reaction zone, coupled with the temperature, preferably is such as to achieve a single phase or supercritical state. Desirably, the pressure throughout the course of the reaction helps maintain the single phase or supercritical state. The pressures applied in the reaction of ammonia with ethylene oxide can be within the range of about 2000 pounds per square inch absolute (psia) to about 5000 pounds per square inch absolute (psia).

In general, if the pressure of the reaction zone is increased, then there tends to be a consequent increase in the reaction rate. An increase in pressure can be reflected by an increase in the density of the supercritical material. In the typical case, the density of the single phase supercritical material can be at least 15 pounds per cubic foot (240 kilograms per cubic meter).

A desirable process from the standpoint of this invention is one which produces a mixture of ethanolamines, whereby monoethanolamine is present in an amount greater than 50 weight percent of the total concentration of ethanolamines. One preferred product mixture includes at least 70 percent monoethanolamine by weight of the ethanolamines and relatively small amounts of the diethanolamine and triethanolamine.

The reaction between ethylene oxide and ammonia forms an effluent which includes one or more ethanolamines, unreacted ammonia, any other unreacted components (e.g., water and the like), and optionally one or more of reaction byproducts. According to the invention, the number of unit operations (e.g., ammonia recovery units, water removal units, and the like) in the overall process scheme of forming ethanolamines and ethyleneamines from ethylene oxide and ammonia can advantageously be reduced or minimized depending on how the effluent from the ethylene oxide and ammonia is subsequently handled. Said effluent can provide at least part of the feed for the reaction between one or more ethanolamines and ammonia to produce one or more ethyleneamines, discussed below.

The reaction to form ethyleneamines from ethanolamines can occur via reductive amination or a condensation reaction. Preferably, the reaction occurs via reductive amination. Reductive amination is the process by which ammonia or an amine is condensed with aldehydes or ketones to form imines which are subsequently reduced to amines. The amination of ethanolamines to ethyleneamines is generally regarded as a reductive amination since it is believed that the ethanolamine initially undergoes a dehydrogenation to form the aldehyde which subsequently reacts with ammonia or an amine to form the imine which is reduced to the amine. Reductive amination is also disclosed in U.S. Provisional Patent Application titled "METHODS OF MAKING CYCLIC, N-AMINO FUNCTIONAL TRIAMINES" by Stephen W. King, having Ser. No. 61/195,412, bearing, and filed on Oct. 6, 2008, the entirety of which reference is incorporated herein by reference.

In reductive amination, one or more ethanolamines can be reacted with ammonia to form one or more ethyleneamines. Ethyleneamines are well known in the art and include ethylenediamine (EDA), diethylenetriamine (DETA), triethylenetetramine (TETA), tetraethylenepentamine (TEPA), piperazine (PIP), aminoethylpiperazine (AEP), aminoethylethanolamine (AEEA), heavy polyamine (HPA), and combinations thereof. HPA is a mixture of linear, branched, and/or cyclic ethyleneamines, the structures of which can be deduced from the chemistry of manufacture and knowledge of the structures present in TETA and TEPA. The structures of the principle components of HPA can contain six or more nitrogen atoms per molecule.

The reaction mixture of ammonia and one or more ethanolamines (e.g., monoethanolamine, diethanolamine, and/or triethanolamine) can also be referred to as an amination feed stream. Preferably, the feed stream for the amination reaction is a homogeneous fluid stream.

The effluent from the reaction between ethylene oxide and ammonia can serve as at least part of the amination feed stream. Such effluent serving as a feed stream includes at least one or more ethanolamines and unreacted ammonia. Optionally, the effluent can include or be combined with one or more additional components to serve as an amination feed stream. Such optional components include hydrogen gas, water, recycled monoethanolamine, recycled ammonia, fresh ammonia, combinations of these, and the like. In certain embodiments, the entire effluent from the reaction of ethylene oxide and ammonia can be fed to the reaction for forming ethyleneamines.

In further characterizing the amination feed stream, the preferred monoethanolamine content thereof is at least 70 weight percent monoethanolamine based on the total ethanolamines content, even more preferably at least 99.5% of the weight of the total ethanolamines content. Preferably the diethanolamine content of the amination feed stream is at least 0.2% of the weight of the total ethanolamines content, but not more than about 30 weight percent of the total ethanolamines content. Preferably, the triethanolamine content of the amination feed stream is 15% or less by weight of the total ethanolamines content, even more preferably less than 0.1% by weight of the total ethanolamines content. Preferably, the sum of the diethanolamine and triethanolamine does not exceed 30 weight percent of the total ethanolamine content.

In practicing a process of this invention the monoethanolamine in the amination feed stream can come from the ethylene oxide/ammonia reaction effluent, a separate introduction of monoethanolamine (e.g., from a recycle stream as described below), or combinations of thereof. If monoethanolamine is added to the effluent from the ethylene oxide/ammonia reaction, such additional monoethanolamine is preferably provided to the amination zone in admixture with the amination feed stream, and therefore can become a part thereof either immediately prior to the feeding of the amination feed stream to the amination zone or at some point further upstream of the amination zone.

The amination feed stream also contains ammonia in an amount which is preferably in stoichiometric excess of the alcoholic hydroxyl groups which are present in the amination feed stream. Preferably, the ratio of moles of ammonia to mole of ethanolamines is in the range of 5 to 60. In the preferred case there is contained at least 10 moles of ammonia for each mole of ethanolamine present in the amination feed stream. The amount of ammonia that is present for the amination reaction can be subject to the amount of ammonia which is utilized in the reaction with ethylene oxide. In the typical case the amount of ammonia which will be used will be vastly in excess of the stoichiometry of the reaction to produce the product mixture of ethyleneamines and therefore the available ammonia which is used in the reaction between ethylene oxide and ammonia will in large part be adequate for the subsequent amination reaction to produce the ethyleneamines. However, fresh ammonia and/or recycled ammonia can be introduced into the amination feed stream if desired.

Optionally, the amination feed stream may also include an amount of water. The water that is present will typically be that which is provided as a result of the ethylene oxide-ammonia reaction. The water content in the amination feed stream may range between 0 weight percent to 10 weight percent, based on the total weight of the amination feed stream and preferably the water content is kept between 0 to 5 weight percent, based on the total weight of the amination feed stream.

Optionally, hydrogen may be supplied as a separate feed stream into the amination zone (discussed below) or as a component of the amination feed stream. Hydrogen can serve the purpose of maintaining catalyst activity and selectivity. When hydrogen is not provided in the reaction zone and the catalyst is a nickel-rhenium catalyst as described below, the catalyst life can be greatly shortened and the rate of amine production can be significantly reduced. By providing hydrogen in the amination zone, the catalyst can be continuously promoted to effectively cause the amination of the ethanolamines to produce the desired ethyleneamine products. While not being bound by theory, it is believed that hydrogen acts in part to keep available sites at the catalyst surface for the desired reaction between ammonia and the ethanolamines and preclude the stabilization of the catalyst sites by ethyleneamines and/or ammonia, and/or formation of metal nitrides.

As a promoter for the catalyst, hydrogen is preferably present in the amination feed stream in an amount in the range of from about 0.0001 mole percent to about 30 mole percent based on the total moles in the amination feed stream. Preferably the amount of hydrogen which is provided in the amination feed stream is from about 0.001 to about 2 mole percent based on the total moles in the amination feed stream.

Optionally, a hydrogenation zone can be added to the reductive amination reactor to reduce color precursor impurities prior to introduction to the reductive amination catalyst. Additionally, a hydrogenation zone can prevent alkylamines present in recycled ammonia from entering a reductive amination process.

Optionally, one or more inert components can also be supplied to the amination zone. Inert gases can help to control the reaction temperature and/or assist in maintaining the desired pressure conditions during the course of the reaction. Suitable inert gases include gases such as nitrogen, helium, methane, and the like. Inert solid materials can serve the purpose of adequately diluting the catalyst bed for the purpose of controlling gas flow characteristics within the catalyst bed as well as assisting in the control of the temperature within the amination zone. Suitable inert solid diluents for the catalyst can be any of the catalyst support materials utilized in the manufacture of the catalyst (discussed below) and preferably are selected from among alpha-alumina, silicon carbide, silica, glass shot or balls, and the like.

The amination zone includes a catalyst material to effect the amination reaction and convert the amination feed stream into an effluent stream that includes at least one or more ethanolamines and one or more ethyleneamines. Such material effects the product mix of the ethyleneamines.

Suitable catalysts include heterogeneous catalysts that have one or more metals selected from the group consisting of nickel (Ni), cobalt (Co), copper (Cu), ruthenium (Ru), rhenium (Re), rhodium (Rh), palladium (Pd), platinum (Pt), and combinations thereof, on a carrier selected from the group consisting of aluminum (Al), titanium (Ti), zirconium (Zr), silicon (Si), and combinations thereof. Though the catalysts which are generally described in the prior art as capable of converting a mixture of ammonia and monoethanolamine to ethylenediamine may be utilized in the practice of this invention, one preferred catalyst is a solid material including nickel and rhenium on a support. Such catalysts are described in the U.S. Pat. No. 4,123,462 (Best), U.S. Pat. No. 4,111,840 (Best), and U.S. Pat. No. 6,534,441 (Bartley et al.).

In preferred embodiments, the reductive amination process is carried out in such a manner as to favor the selectivity of the reaction towards the production of ethylenediamine. This can be accomplished by utilizing the well-known nickel-rhenium catalysts which are described in the U.S. Pat. No. 4,123,462 (Best), U.S. Pat. No. 4,111,840 (Best), and U.S. Pat. No. 6,534,441 (Bartley et al.).

A particularly preferred catalyst is a selective and stable catalyst that includes nickel/rhenium catalyst supported on an $Al_2O_3$—$SiO_2$ carrier. Such a catalyst is described in U.S. Pat. No. 6,534,441 (Bartley et al.). Such a catalyst includes nickel and rhenium as active metals. More particularly, the catalyst can include from about 2 to about 75 weight percent nickel and has a nickel to rhenium weight percent ratio of from about 1:1 to about 200:1. The catalyst is preferably supported on an alumina-silica support which contains from about 5 to about 65 weight percent silica and preferably has a BET surface area of from about 30 to about 450 square meters per gram. The catalyst optionally includes boron and preferably has a boron to nickel weight percent ratio less than or equal to about 1. The nickel content of the catalyst, the nickel to rhenium and boron to nickel weight percent ratios, the support surface area, and the silica content of the support can be selected to provide the catalyst composition with a specified activity, and to provide a particular mix of amine products.

Such catalyst shows significantly improved selectivity to ethylenediamine. Advantageously, such catalyst can achieve such improved selectivity at relatively moderate temperature and pressure conditions. For example, such catalyst can achieve the desired product selectivity at a temperature in the range of from 155° C. to 160° C. and a pressure of 3000 psig or less.

Other useful catalysts for reductive amination include nickel and rhenium catalysts as described in co-pending U.S. Provisional Patent Application titled "LOW METAL CATALYST COMPOSITIONS INCLUDING ACIDIC MIXED METAL OXIDE AS SUPPORT" by Stephen W. King et al., having Ser. No. 61/195,455, bearing, and filed on Oct. 6, 2008, the entirety of which reference is incorporated herein by reference. Yet other useful catalysts for reductive amination include catalysts having nickel, cobalt, or copper, or combinations thereof as described in co-pending U.S. Provisional Patent Application titled "LOW METAL LOADED, ALUMINA SUPPORTED, CATALYST COMPOSITIONS AND AMINATION PROCESS" by Stephen W. King et al., having Ser. No. 61/195,434, bearing, and filed on Oct. 6, 2008, the entirety of which reference is incorporated herein by reference.

The reaction which involves the amination feed stream to produce ethyleneamines is accomplished in the amination zone. This zone contains the solid catalyst preferably in the form of a fixed bed and has a temperature and pressure sufficient to cause the amination feed stream to react to form the ethyleneamines. The amination zone includes the appropriate catalysts for the amination reaction, as described above, and the amination feed stream.

As mentioned above, the catalyst is provided in the amination zone preferably in the form of a bed of particles. Typically, such beds are supported upon distribution plates or screens which allow for the passage of gases or other fluids through the bed. In this respect, the process can be carried out utilizing standard fluid-solid heterogeneous catalytic techniques.

In the preferred operation of a process of this invention the amination feed stream is supplied to the amination reaction as a single phase or supercritical stream. The pressure of supercritical amination feed stream can be equal to or less than the pressure of the continuous homogeneous fluid stream (effluent) which is removed from the reaction between ethylene oxide and ammonia. Consequently, the amination reaction zone is at a pressure which is essentially equivalent to the pressure of the amination feed stream as it exists when introduced to the amination reaction zone. Typically, the pressure of supercritical amination feed stream is less than the pressure of the continuous homogeneous fluid stream (effluent) which is removed from the reaction between ethylene oxide and ammonia, even though the amination feed stream is also preferably a single phase or supercritical stream. Alternatively, the amination feed stream can be supplied to the amination reaction as a two-phase fluid stream.

Preferably, the stream within the amination zone is under supercritical or liquid phase conditions, preferably under supercritical conditions as described above. Therefore, the pressure within the reaction zone can be correlated with the temperature so as to achieve either the supercritical conditions, mixed liquid/vapor phase conditions, a vapor phase condition, or a liquid phase condition. In preferred embodiments, liquid phase or supercritical phase conditions are selected. If carrying out the amination reaction process with a preferred nickel-rhenium catalyst which also contains boron, as described in U.S. Pat. No. 6,534,441 (Bartley et al.), the pressure is preferably in the range of about 1000-4000 psia, even more preferably in the range of from 1500-3000 psia. When operating at such pressures, the temperature is preferably in the range of about 150° C.-215° C. The temperature of the amination zone can also be selected based upon the temperature characteristics of the catalyst which is utilized for the amination reaction. When employing the nickel-rhenium catalyst mentioned above, this temperature can be in the range of from 120° C. to about 225° C., preferably in a range of about 150° C. to about 215° C. The reactor space velocities can be in the range of 2-50 moles of ethanolamines per kilogram of catalyst per hour, preferably in the range of 10-20 moles of ethanolamines per kilogram of catalyst per hour.

The amination reactor which provides the amination zone may be any reactor configuration, a fixed bed plug flow reactor being preferred. The reductive amination reactor can be up-flow or down-flow and is preferably designed to minimize back mixing.

The conversion of ethanolamines by the reductive amination reaction can be in the range of from 20% to 80%, preferably in the range of from 30% to 50%. In certain embodiments, the reductive amination reaction has a relatively high selectivity for ethylenediamine (e.g., yields of greater than 90%).

Figure 2:
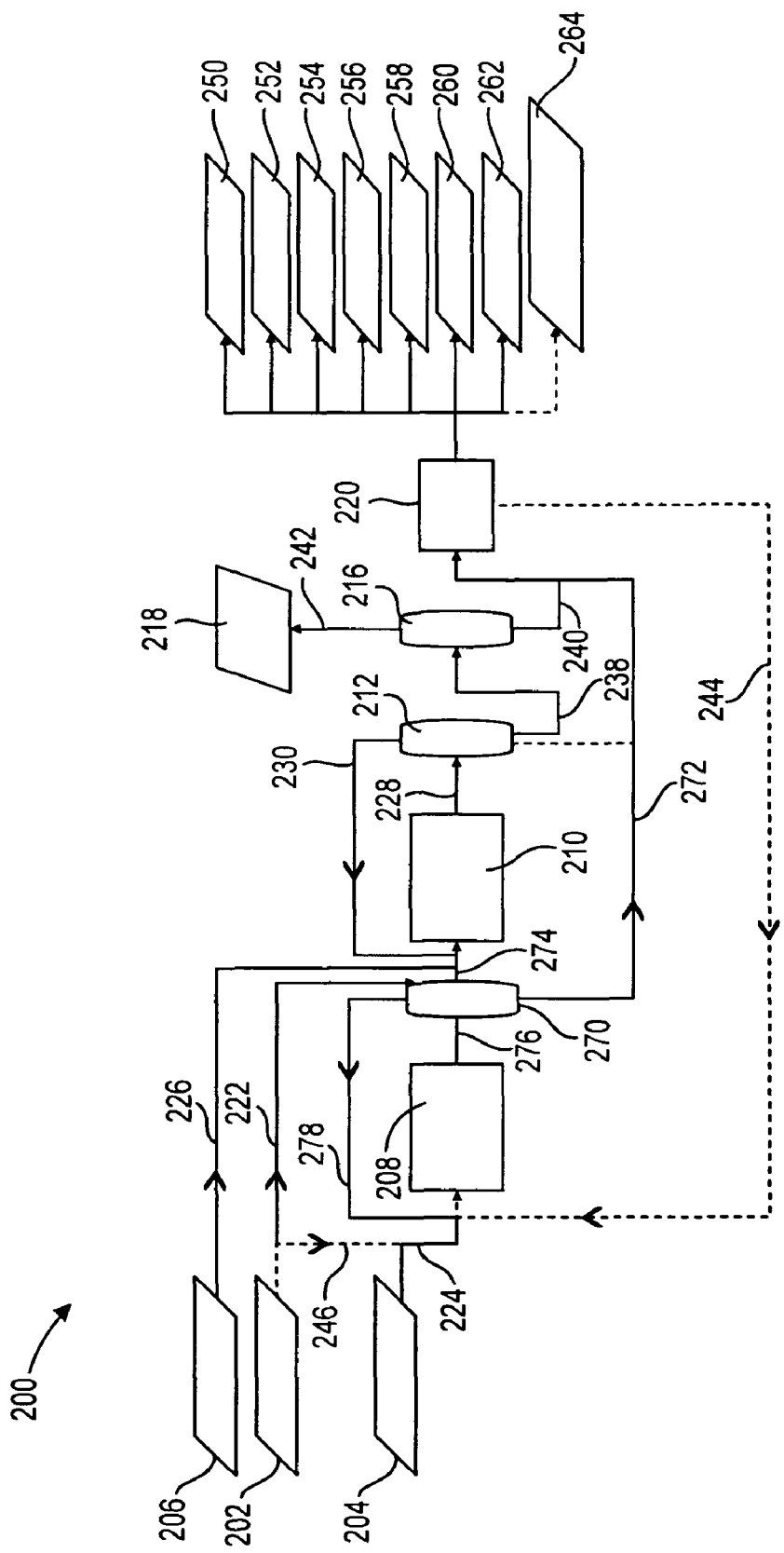
FIG. 2 shows a schematic flow diagram of an alternative embodiment for preparing ethanolamines and ethyleneamines from ethylene oxide and ammonia according to the present invention.
Figure 3:
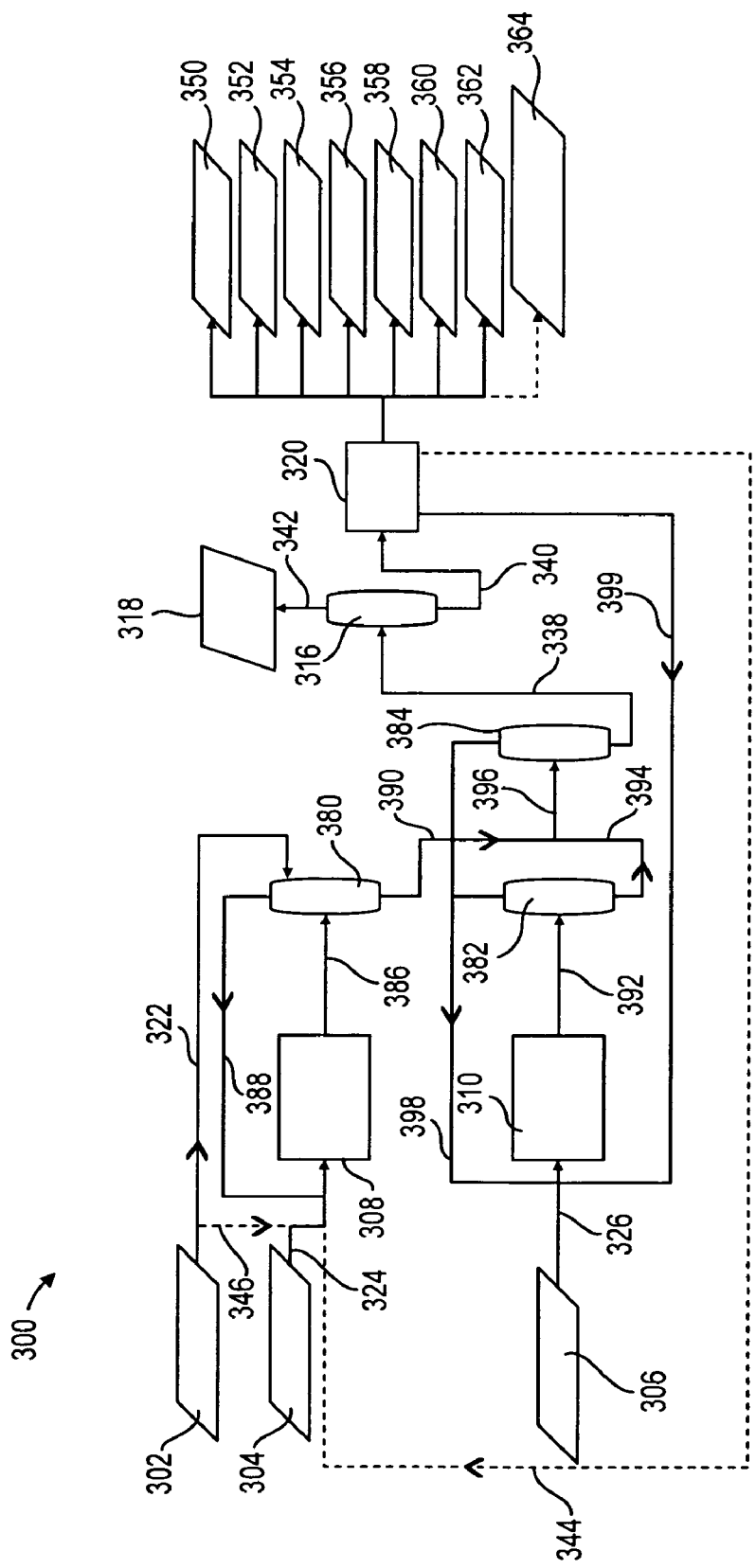
FIG. 3 shows a schematic flow diagram of an alternative embodiment for preparing ethanolamines and ethyleneamines from ethylene oxide and ammonia according to the present invention.

The effluent from the reaction of one or more ethanolamines and ammonia can be fed to any desired unit operation. Preferably, as described below, the effluent is subjected to a variety of separation steps for the purpose of removing the various components contained therein. For example, in one embodiment, the effluent stream from the amination zone can be subjected to several separation steps to remove water, ammonia, ethylenediamine, monoethanolamine (which can be recycled back to the reactor producing the ethanolamines or the reactor producing the ethyleneamines), aminoethylethanolamine, diethylenetriamine, piperazine, amine heavies, diethanolamine, and triethanolamine. "Amine heavies" refers to ethyleneamines having a boiling point greater than TETA at the pressure at which the amines are being refined. In preferred embodiments, the effluent is fed to one or more unit operations in a manner that relatively reduces the overall number of unit operations needed to manufacture ethanolamines and ethyleneamines from ethylene oxide and ammonia. For example, FIGS. 1-3 are discussed below and illustrate process schemes according to the invention that can help minimize the overall number of unit operations for producing ethanolamines and ethyleneamines from an initial reaction of ethylene oxide and ammonia.

One or more ammonia recovery systems can be used in the process of making ethanolamines and ethyleneamines from ethylene oxide and ammonia. An ammonia recovery system separates ammonia, and optionally one or more additional components, from a fluid stream. An ammonia recovery system can be positioned anywhere in the overall process as desired. Preferably, one or more ammonia recovery systems are used in a manner that minimizes the number of ammonia recovery systems, unit operations (e.g., distillation columns, pumps, heat exchangers) and/or other process units (e.g., alkylamine removal systems, discussed below). The recovered ammonia can be used in any desired manner. For example, depending on the purity level of the recovered ammonia, the recovered ammonia may be recycled to another point in the process such as the inlet of one or more reactors. Advantageously, such recovered ammonia can be used as "make-up" ammonia for reactors where ammonia is consumed in a reaction.

Ammonia recovery systems can be any type of ammonia recovery system known in the art. For example, an ammonia recovery system can utilize distillation columns, multiple single stage separators, compressors, chillers and/or absorbers in many different combinations and the like. Ability to vary the to amount of ammonia entering the amination zone by adding additional ammonia and or removing ammonia provides greater mix capability and mix flexibility in the amination reactor.

When a very high selectivity to ethylenediamine is desired in the amination reactor, the preferred monoethanolamine content of amination feed stream is 99.5% of the ethanolamine content of the amination feed. To help achieve the desired monoethanolamine content, the effluent from the reaction of ethylene oxide and ammonia is preferably introduced into an "inter-reactor separator" ammonia recovery system, preferably a multistage inter-reactor separator. In general, a multistage inter-reactor separator is a standard single shell or dividing wall distillation column containing either trays or packing. This distillation column preferably has a feed zone, a rectifying section or sections, stripping section or sections, a total or partial condenser, and a reboiler. In an inter-reactor separator, the pressure of the homogenous ethylene oxide reactor effluent is reduced well below the critical point of the effluent from the reaction of ethylene oxide and ammonia, the effluent is allowed to flash in the feed zone of the inter-reactor separator. Optionally, the ethylene oxide reactor effluent can be heated (e.g., passed through a heater) before being introduced into the inter-reactor separator. If the effluent is heated prior to being introduced into the "inter-reactor separator," preferably the effluent is heated after the pressure of the effluent is reduced. In the rectifying section, materials heavier than monoethanolamine can be removed from the ethylene oxide reactor effluent and a stream containing ammonia and monoethanolamine leave the rectifying section overhead and go to a condenser. Preferably, the condenser is a partial condenser with conditions set so as to permit essentially pure ammonia (>99% ammonia) to be removed as a vapor stream. Advantageously, the recovered ammonia having such high purity can be recycled to one or more locations in the process to form ethyleneamines from ethanolamines, wherein the ethanolamines are formed from ethylene oxide and ammonia. For example, as discussed below in FIG. 2, an inter-reactor separator 270 having a partial condenser is positioned between reactor 208 and reactor 210 and the purified ammonia is recycled to reactor 208 (the reactor that forms one or more ethanolamines from ethylene oxide and ammonia). The liquid stream from such a partial condenser preferably contains the desired amount of ammonia and the desired amount monoethanolamine at the desired purity and can then be fed to an amination reactor (e.g., reactor 210 in FIG. 2). In one embodiment, the inter-reactor separator can form a "bottoms" stream that includes a small amount of ammonia, water, and monoethanolamine, and all of the diethanolamine and triethanolamine from the ethylene oxide reactor effluent. Preferably, this bottoms stream from the inter-reactor separator can bypass the amination reactor and be fed to a product refining system at the appropriate location in the process to recover the various components. For example, DEA and TEA can be separated from MEA so that the DEA and TEA are not fed to the amination reactor. Preventing DEA and TEA from entering the amination reactor can advantageously improve the selectivity for EDA. Optionally, the inter-reactor separator just described can include one or more additional "side-draws." Additional side-draws permit streams of different compositions to be formed which can permit optimization and further simplification of the downstream product recovery system.

In general, an inter-reactor separator has between 5 and 50 theoretical separation stages with the preferred number of stages being between 15 to 25. The inter-reactor separator can operate at pressures between 50 psi to 700 psi, preferably between 200 to 400 psi. Reboiler temperatures of an inter-reactor separator can range between 150° C. to 225° C., preferably in the range of from 170° C. to 190° C.

Optionally, an ammonia recovery system can be coupled with a water removal system (discussed below), product separation system (discussed below), and combinations of these.

Alkylamines can be present in one or more product streams described herein. Alkylamines are well known and include methylamine, ethylamine, and combinations thereof. For example, alkylamines can be generated as by-products in the reductive amination of monoethanolamine. If ammonia is recovered from an effluent stream that includes alkylamines, at least a portion of the alkylamines tend to be separated with the ammonia. Unfortunately, if the ammonia is recycled back into the process described herein, the alkylamines can impact one or more of product purity and product mix. For example, if alkylamines are recycled with ammonia back into a reactor that makes ethanolamines from ethylene oxide and ammonia (e.g., reactor 108 in FIG. 1), the alkylamines can become ethoxylated, and thereby create new species of impurities that have to be removed. An alkylamine content in the ammonia feeding the ethylene oxide and ammonia reactor is preferably less than 100 parts million by weight, preferably less than 50 parts million by weight, so as to help avoid product quality or separation issues in downstream operations. According to the present invention, alkylamines can be handled in a manner that minimizes their impact on product purity and/or product mix. For example, by coupling an ammonia recovery system (e.g., conventional distillation column) to an alkylamine removal system, the alkylamines can be removed from the ammonia recycle stream. An alkylamine removal system can separate alkylamines from ammonia via membrane, hydrogenolysis, extraction, selective adsorption, selective absorption, precipitation, distillation, combinations of these, and the like. A preferred alkylamine removal system includes distillation. Alkylamines that are separated from ammonia can be, e.g., sold, sent to waste treatment, or recycled to a reductive amination reactor. As another example of processing alkylamines in a manner that minimizes their impact on product purity and/or product mix, appropriate ammonia recycling schemes can be selected so ammonia can be recycled to desired destinations (e.g., reactors 208 and 210 in FIG. 2 and reactors 308 and 310 in FIG. 3), yet the alkylamines are prevented from being recycled into a reactor that makes ethanolamines (e.g., reactors 208 and 308).

As mentioned above, water can be present in one or more product streams described herein. For example, water is a normal co-product of a process used to produce ethyleneamines via reductive amination of monoethanolamine. Thus, a process according to the present invention can have a water removal system to remove water from one or more products so that the product stream can be further refined. Typically, water is removed from an amines rich stream and the water is then sent to a waste water treatment system. A water removal system can be positioned anywhere in the overall process as desired. Preferably, one or more water removal systems are used in a manner that minimizes the number of such systems. A preferred water removal system includes conventional distillation. However, as discussed below in connection with FIG. 4 and alkylethyleneamines, a water column according to the present invention can be used to remove alkylethyleneamines in addition to water.

Alkylethyleneamines can be present in one or more product streams described herein. For example, water, N-Methylethylenediamine and N-Ethylethylenediamine are normal co-products of a process used to produce ethyleneamines via reductive amination of monoethanolamine. Preferably, ethylenediamine is sold or used as a relatively pure product (99.5% purity minimum) with a water specification of 0.3 wt % maximum. Certain applications specifications have a N-Methylethylenediamine and N-Ethylethylenediamine content at less than 1000 ppm total. Due to the formation of water in the ethyleneamines process, water is preferably removed to produce salable ethylenediamine. In some instances, a portion of both N-Methylethylenediamine and N-Ethylethylenediamine are also preferably removed from the product.

Since water and ethylenediamine can form an azeotrope, separation by refining can be difficult. Typical industry practice is to use pressure to break the ethylenediamine water azeotrope and operate the water column at a high enough pressure to allow ethyleneamines to leave the base of the column essentially free of water. Operating the water column in this manner allows water containing a small amount of amine (primarily ethylenediamine) to be removed overhead. The ethyleneamines product stream containing a small amount of water exits from the base of the column. The material from the base of the water column then goes to a second column where ethylenediamine, N-Methylethylenediamine, N-Ethylethylenediamine and the remaining water are removed overhead and the rest of the ethyleneamines products leaves the base. Such an operation produces an ethylenediamine product that is suitable for most applications but typically contains more than 2000 ppm of N-Methylethylenediamine and N-Ethyl-ethylenediamine, which although meets industry specifications can be unacceptable for certain high purity applications. However, once the N-Methylethylenediamine and N-Ethylethylenediamine co-products are in the ethylenediamine product they can be extremely difficult to remove and further purification is typically not practical. It has been discovered that a unique azeotropic interaction between water, ethylenediamine, N-Methylethylenediamine, and N-Ethylethylenediamine allows N-Methylethylenediamine and N-Ethylethylenediamine to be preferentially removed in a water column via the overhead water product, while the ethylenediamine leaves the base. To help accomplish this separation, the water column operating pressure, feed location, and number of stages in the water column are adjusted so as to form and azeotrope with Methylethylenediamine, N-Ethylethylenediamine, and water.

In one embodiment, a process for separating one or more alkylethylenediamines from ethylenediamine includes the steps of: a) providing a composition including: i) ethylenediamine; ii) water; and iii) one or more alkylethylenediamines; b) causing the composition to be subjected to conditions such that an azeotrope forms between the water and the one or more alkylethylenediamines; and c) separating the one or more alkylethylenediamines and at least a portion of the azeotropic water from the composition. Preferably, after the step of separating the one or more alkylethylenediamines and at least a portion of the azeotropic water from the composition, the amount of alkylethylenediamines present in the composition is less than 1000 parts per million by weight. In certain embodiments, a process for the manufacture of ethylenediamine includes the steps of: a) reacting monoethanolamine with ammonia in the presence of a reductive amination catalyst to produce at least ethylenediamine, wherein said reaction produces water and one or more alkylethylenediamines as by-products, wherein said reacting step forms an effluent including: i) the ethylenediamine; ii) the water; and iii) the one or more alkylethylenediamines; b) causing the effluent to be subjected to conditions such that an azeotrope forms between the water and the one or more alkylethylenediamines; c) separating the one or more alkylethylenediamines and at least a portion of the azeotropic water from the effluent. Preferably, the step of causing the effluent to be subjected to conditions such that an azeotrope forms between the water and the one or more alkylethylenediamines also causes an azeotrope to form between water and ethylenediamine, and further including the step of, after separating the one or more alkylethylenediamines, separating the water from the ethylenediamine. Preferably, after the step of separating the one or more alkylethylenediamines and at least a portion of the azeotropic water from the effluent, the amount of alkylethylenediamines present in the effluent is less than 1000 parts per million by weight.

In another embodiment, a process for the manufacture of one or more ethyleneamines includes the steps of: a) reacting monoethanolamine with ammonia in the presence of a reductive amination catalyst to produce one or more ethyleneamines, wherein said reaction also produces water and one or more alkylethyleneamines as by-products, and wherein said reacting step forms an effluent including: i) the one or more ethyleneamines; ii) the water; and iii) the one or more alkylethyleneamines; b) causing the effluent to be subjected to conditions such that an azeotrope forms between the water and the one or more alkylethyleneamines; and c) separating the one or more alkylethyleneamines and at least a portion of the azeotropic water from the effluent. Preferably, the step of reacting monoethanolamine with ammonia in the presence of a reductive amination catalyst produces ethylenediamine and one or more additional ethyleneamines, wherein the effluent further includes said one or more additional ethyleneamines, and further including the step of, prior to step (b), separating the one or more additional ethyleneamines from the effluent. Preferably, after the step of separating the one or more alkylethyleneamines and at least a portion of the azeotropic water from the effluent, the amount of alkylethyleneamines present in the effluent is less than 1000 parts per million by weight.

Figure 4:
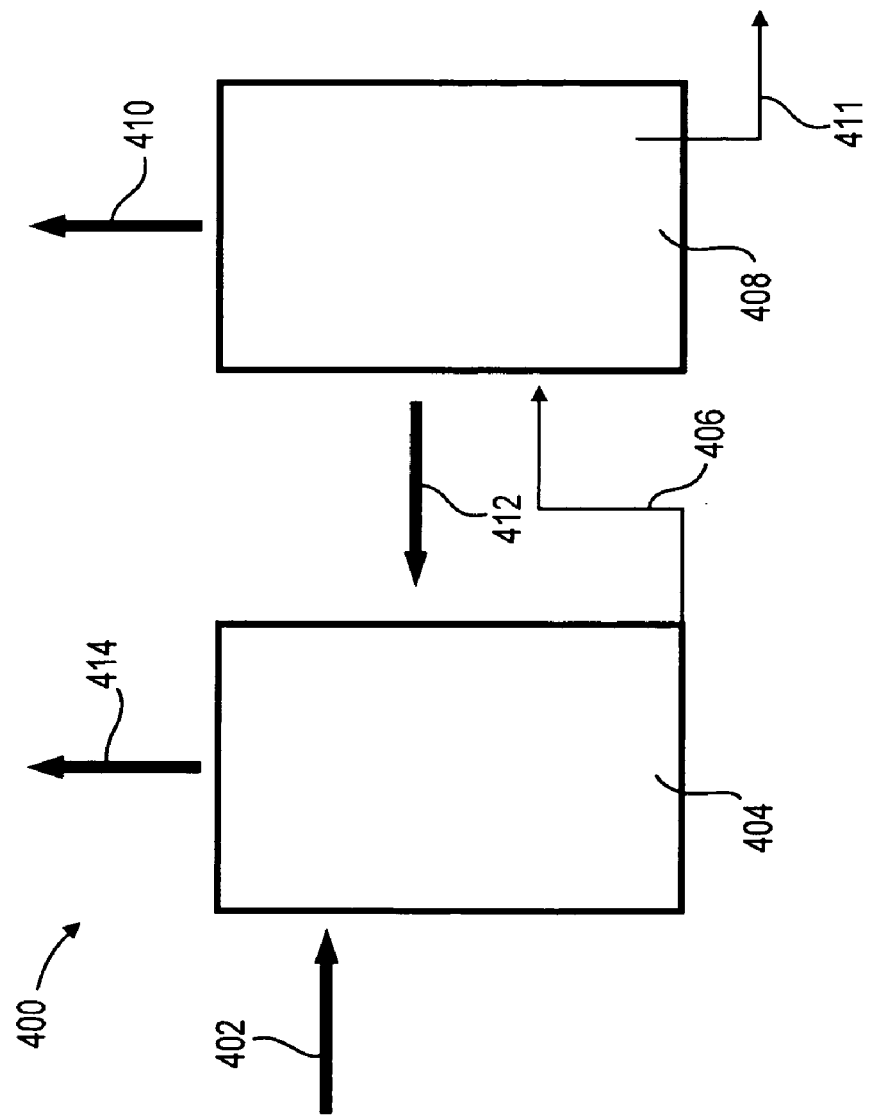
FIG. 4 shows a schematic flow diagram of one embodiment for separating one or more alkylethylenediamines from ethylenediamine according to the present invention.

This idea is further illustrated by reference to an exemplary schematic flow diagram shown in FIG. 4. System 400 has water column 404, preferably a distillation column, and an ethylenediamine column 408, preferably a distillation column. The water column feed 402 is introduced to water column 404 at a location where preferably approximately 20% of the stages are rectifying stages and 80% are stripping stages. The water column feed 402 preferably includes a mixture of ethanolamines and ethyleneamines, wherein the mixture is substantially free of ammonia. Typically, the feed 402 will be downstream of an ammonia removal process (e.g., after ammonia recovery unit 112 in FIG. 1, after ammonia recovery unit 212 in FIG. 2, or after ammonia recovery unit 384 in FIG. 3). In preferred embodiments, water column 404 is operated at a pressure in the range of from 14.7 to 30.7 psia, even more preferably at a pressure in the range of from 21.7-28.7 psia. Because operating pressure, feed location in column 404, and number of stages in the water column 404 are appropriately selected, N-Methylethylenediamine and N-Ethylethylenediamine form an azeotrope with water allowing a significant portion of the N-Methylethylenediamine, N-Ethylethylenediamine, and water to be readily separated from the ethanolamines and ethyleneamines and go overhead with the water via stream 414. The ethanolamines and ethyleneamines leave column 404 via stream 406. Because the water column 404 operating pressure is below the pressure required to break the azeotrope between ethylenediamine and water azeotrope, the bottom stream 406 of water column 404 typically contains more water than is desired in the ethylenediamine product. The remainder of this water is then removed from the ethanolamines and ethyleneamines in the ethylenediamine column 408 via a water rich side draw 412 which is recycled back to the water column 404 at an optimum feed location that is typically in the feed zone or below the main water column feed 402. Relatively pure EDA product is separated and leaves column 408 via stream 410 and the remaining amines heavier than EDA leave column 408 via stream 411.

Operating conditions, feed locations, side draw locations, and number of stages in the water column 404 and ethylenediamine column 408 are all variables that can be optimized based on the composition of an effluent or effluents from one or more reactors in order to remove N-Methylethylenediamine and N-Ethylethylenediamine with minimal energy and capital input.

The one or more ethanolamines and one or more ethyleneamines made by a process according to the present invention can be separated (refined) by any method known in the art. For example, the ethanolamines and ethyleneamines can be refined using conventional distillation technology known in the art. Preferably, dividing wall columns are used.

One or more ethanolamine products from product refining can be recycled to the reactor that makes ethanolamines so as to help provide additional mix flexibility.

One or more ethyleneamine products from product refining can be recycled to the reactor that makes ethyleneamines so as to help provide additional mix flexibility.

Optionally, the ethanolamines and ethyleneamines can be subjected to a color treatment process so as to improve product quality. The treatment of compounds which have color impurities is well known. One approach is to use a reducing agent, such as sodium borohydride or hydrogen in the presence of a suitable catalyst, such as Pd or Pt. Other chemicals that have been used include hydrazine, hydroxylamine, and aminoalcohols. Color removal has also been performed by treatment with activated carbon, or by redistillation. Ion exchange resins, diatomaceous earths, clays, and zeolitic materials have also been used to remove color impurities. A combination of water and acids (carbon-dioxide and inorganic acids) has been reported to remove color (see U.S. Pat. No. 6,222,008). In addition, acids or bases may be added followed by distillation to give improved color (see U.S. Pat. No. 3,847,754). A combination of these methods has also been employed to remove color impurities (see U.S. Pub. No. 2006/0030726). Preferably, color treatment is performed by rigorous exclusion of air and metallic impurities. Optionally, a color treatment system can be included within a product refining section.

Optionally, one or more wastewater treatment unit operations can be used in a process according to the present invention to treat wastewater.

Optionally, the effluent from the reactor that forms one or more ethyleneamines via reductive amination can be coupled (e.g., directly fed to) with a transamination reactor so as to adjust the product mix of ethyleneamines as desired. See co-pending U.S. Provisional Patent Application titled "METHOD OF MANUFACTURING ETHYLENEAMINES" by David M. Petraitis et al., having Ser. No. 61/195,454, bearing, and filed on Oct. 6, 2008, the entirety of which reference is incorporated herein by reference. Transamination is also disclosed in U.S. Provisional Patent Application titled "METHODS OF MAKING CYCLIC, N-AMINO FUNCTIONAL TRIAMINES" by Stephen W. King, having Ser. No. 61/195,412, bearing, and filed on Oct. 6, 2008, the entirety of which reference is incorporated herein by reference. See also, co-pending U.S. Provisional Patent Application titled "A PROCESS TO SELECTIVELY MANUFACTURE DIETHYLENETRIAMINE (DETA) OR OTHER DESIRABLE ETHYLENAMINES VIA CONTINUOUS TRANSAMINATION OF ETHYLENEDIAMINE (EDA), AND OTHER ETHYLENEAMINES OVER A HETEROGENEOUS CATALYST SYSTEM" by Ronald Gary Cook et al., having Ser. No. 61/195,404, bearing, and filed on Oct. 6, 2008, the entirety of which reference is incorporated herein by reference. A preferred catalyst for said transamination reactor includes nickel and rhenium as described in co-pending U.S. Provisional Patent Application titled "LOW METAL CATALYST COMPOSITIONS INCLUDING ACIDIC MIXED METAL OXIDE AS SUPPORT" by Stephen W. King et al., having Ser. No. 61/195,455, bearing, and filed on Oct. 6, 2008, the entirety of which reference is incorporated herein by reference. And yet another preferred catalyst for said transamination reactor includes a catalyst having nickel, cobalt, or copper, or combinations thereof as described in co-pending U.S. Provisional Patent Application titled "LOW METAL LOADED, ALUMINA SUPPORTED, CATALYST COMPOSITIONS AND AMINATION PROCESS" by Stephen W. King et al., having Ser. No. 61/195,434, bearing, and filed on Oct. 6, 2008, the entirety of which reference is incorporated herein by reference.

In certain embodiments, by directly feeding the effluent from a reductive amination reaction to a transamination reaction, a product mix rich in DETA and TETA can be produced.

The present invention will now be further illustrated by reference to the three exemplary schematic flow diagrams shown in FIGS. 1-3. It is noted that dashed lines in FIGS. 1-3 represent optional flow pathways.

FIG. 1 shows schematic flow diagram of a process 100 according to the present invention for preparing ethanolamines and ethyleneamines from ethylene oxide and ammonia. A source of ethylene oxide 104 is combined with recycled ammonia and water via streams 124 and 134, respectively, and fed to a homogeneously catalyzed reactor 108 to form an effluent 136 of unreacted ammonia, monoethanolamine, diethanolamine, and triethanolamine. The reactor 108 is set to maintain a single-phase operation. Optionally, a source of fresh ammonia 102 and a source of hydrogen gas 106 can be combined with the ethylene oxide via streams 146 and 148, respectively. All of the effluent from reactor 108 is combined with hydrogen gas from source 106 via stream 126 and fed to reactor 110 to form ethylenediamine, diethylenetriamine, piperazine, amine heavies, and, aminoethylethanolamine. Optionally, before being fed to reactor 110, the effluent from reactor 108 can be cooled via a conventional cooler or integrated process/process heat exchanger (not shown) if additional control of the reaction in reactor 110 is desired. The reactor 110 is preferably a fixed bed reactor containing a heterogeneous catalyst. The pressure in reactor 110 is set to maintain a single-phase operation. The effluent from reactor 110 includes at least ethanolamines (monoethanolamine, diethanolamine, triethanolamine), ethyleneamines (ethylenediamine, diethylenetriamine, piperazine, amine heavies, and, aminoethylethanolamine), water, ammonia, and alkylamines. All of the effluent from reactor 110 is fed to an ammonia recovery unit 112 via stream 128. In this particular embodiment, fresh ammonia from source 102 is also fed to the ammonia recovery unit 112, which is preferably a conventional distillation system, via stream 122. Ammonia and alkylamines are sent overhead from recovery unit 112 and delivered to alkylamine recovery unit 114 via stream 130. Alkylamine removal unit 114 preferably removes 75% to 100% of the alkylamines from process 100. Advantageously, undesirable reactions in reactors 108 and/or 110 with the alkylamines that might otherwise occur (e.g., to produce alkylethylenediamines in reactor 110) are minimized by using removal unit 114. Preferably, alkylamine removal unit 114 is a conventional distillation unit. As shown, purified ammonia is combined with ethylene oxide via stream 134 and the alkylamines are sent to a wastewater treatment system 118 via line 132. The amines (ethyleneamines and ethanolamines) rich stream is sent from the bottom of the ammonia recovery unit 112 to the water removal system 116 via stream 138. Water is preferably removed from the amines rich stream via conventional distillation. The water is sent overhead to the wastewater treatment system 118 via stream 142 and the amines are sent to the product refining system 120 via stream 140 (preferably conventional distillation using dividing wall columns). As shown, product refining system 120 separates the amines into eight products: monoethanolamine product 150, diethanolamine product 152, triethanolamine product 154, ethylenediamine product 156, piperazine product 158, diethylenetriamine product 160, amine heavies 162, and aminoethylethanolamine product 164. To the extent any alkylethyleneamines are present in stream 138, said alkylethyleneamines can be removed with the water in system 116 via the azeotropic method described above in connection with FIG. 4 and sent to wastewater treatment system 118 or said alkylethyleneamines can be sent to the product refining system 120. For example, if alkylethylenediamines are sent to product refining system 120, said alkylethylenediamines typically end up in the ethylenediamine product.

FIG. 2 shows an alternative schematic flow diagram of a process 200 according to the present invention for preparing ethanolamines and ethyleneamines from ethylene oxide and ammonia. A source of ethylene oxide 204 is combined with recycled ammonia and water via stream 278 and fed to a homogeneously catalyzed reactor 208 to form an effluent of unreacted ammonia, monoethanolamine, diethanolamine, and triethanolamine. The reactor 208 is set to maintain a single-phase operation. Optionally, a source of fresh ammonia 202 can be combined with the ethylene oxide via stream 246. All of the effluent from reactor 208 is fed to inter-reactor separator 270 via stream 276 (preferably a conventional distillation column or dividing wall column). In addition, fresh ammonia from source 202 is fed into inter-reactor separator 270 via stream 222. The inter-reactor separator 270 separates the effluent from reactor 208 into three streams. Stream 278 includes ammonia and is recycled so as to be combined with ethylene oxide in stream 224. Stream 274 includes ammonia and monoethanolamine and is fed to reactor 210. Stream 272 includes monoethanolamine, diethanolamine, and triethanolamine and is fed to product refining system 220. Optionally, stream 272 can also contain water and small amounts of ammonia depending and stream 272 can be fed to the ammonia recovery system 212. Hydrogen gas from source 206 is combined with stream 274 via stream 226 and fed to reactor 210 to form ethylenediamine, diethylenetriamine, piperazine, amine heavies, and, aminoethylethanolamine. The reactor 210 is preferably a fixed bed reactor containing a heterogeneous catalyst. The pressure in reactor 210 is set to maintain a single-phase operation. The effluent from reactor 210 includes at least ethanolamines (monoethanolamine, diethanolamine, triethanolamine), ethyleneamines (ethylenediamine, diethylenetriamine, piperazine, amine heavies, and, aminoethylethanolamine), water, ammonia, and alkylamines. All of the effluent from reactor 210 is fed to an ammonia recovery unit 212 (preferably conventional distillation) via stream 228. Ammonia and alkylamines are sent overhead from recovery unit 212 and recycled to reactor 210 via stream 230. Advantageously, undesirable reactions in reactor 208 with the alkylamines that might otherwise occur (e.g., ethoxylation of the alkylamines) are avoided by using recycle stream 278 for reactor 208 and recycle stream 230 for reactor 210 because alkylamines are created in reactor 210, not reactor 208. The amines (ethyleneamines and ethanolamines) rich stream is sent from the bottom of the ammonia recovery unit 212 to the water removal system 216 via stream 238. Water can be removed from the amines rich stream preferably via conventional distillation. The water is sent overhead to the wastewater treatment system 218 via stream 242 and the amines are sent to the product refining system 220 via stream 240 (preferably conventional distillation using dividing wall columns). As shown, product refining system 220 separates the amines into eight products: monoethanolamine product 250, diethanolamine product 252, triethanolamine product 254, ethylenediamine product 256, piperazine product 258, diethylenetriamine product 260, amine heavies 262, and aminoethylethanolamine product 264. Optionally, it may be deemed that aminoethylethanolamine may not exist in quantities sufficient enough to warrant investment for recovery and thus will be recovered with amine heavies 262. To the extent any alkylethyleneamines are present in stream 238, said alkylethyleneamines can be removed with the water in system 216 via the azeotropic method described above in connection with FIG. 4 and sent to wastewater treatment system 218 or said alkylethyleneamines can be sent to the product refining system 220. For example, if alkylethylenediamines are sent to product refining system 220, said alkylethylenediamines typically end up in the ethylenediamine product. Optionally, at least a portion of monoethanolamine separated in refining system 220 can be recycled and introduced into reactor 208.

FIG. 3 shows an alternative schematic flow diagram of a process 300 according to the present invention for preparing ethanolamines and ethyleneamines from ethylene oxide and ammonia. A source of ethylene oxide 304 is combined with recycled ammonia and water via stream 388 and fed to a homogeneously catalyzed reactor 308 to form an effluent of unreacted ammonia, monoethanolamine, diethanolamine, and triethanolamine. The reactor 308 is set to maintain a single-phase operation. Optionally, a source of fresh ammonia 302 can be combined with the ethylene oxide via stream 346. All of the effluent from reactor 308 is fed to an ammonia recovery system 380 via stream 386 (preferably a conventional distillation column or dividing wall column). In addition, fresh ammonia from source 302 is fed into ammonia recovery system 380 via stream 322. The ammonia recovery system 380 separates the effluent from reactor 308 into two streams. Stream 388 includes ammonia and is recycled so as to be combined with ethylene oxide in stream 324. Stream 390 includes ammonia, water, monoethanolamine, diethanolamine, and triethanolamine and is combined with stream 394 and fed to ammonia recovery system 384 via stream 396. Hydrogen gas from source 306 is combined with streams 398 and 399 and fed to reactor 310 via stream 326 to form ethylenediamine, diethylenetriamine, piperazine, amine heavies, and aminoethylethanolamine. Stream 398 includes ammonia from ammonia recovery system 384 and stream 399 includes monoethanolamine from product refining system 320. The reactor 310 is preferably a fixed bed reactor containing a heterogeneous catalyst. The pressure in reactor 310 is set to maintain a single-phase operation. The effluent from reactor 310 includes at least monoethanolamine, ethyleneamines (ethylenediamine, diethylenetriamine, piperazine, amine heavies, and, optionally, aminoethylethanolamine), water, ammonia, and alkylamines. All of the effluent from reactor 310 is fed to an ammonia recovery unit 382 (preferably conventional distillation) via stream 392. Ammonia and alkylamines are sent overhead from recovery unit 382 and recycled to reactor 310 via stream 398. Advantageously, undesirable reactions in reactor 308 with the alkylamines that might otherwise occur (e.g., ethoxylation of the alkylamines) are avoided by using recycle stream 388 for reactor 308 and recycle stream 398 for reactor 310 because alkylamines are created in reactor 310, not reactor 308. The amines (ethyleneamines and ethanolamines) rich stream 394 from the bottom of the ammonia recovery unit 382 is combined with the amines rich stream 390 of ammonia recovery unit 380 and sent to final ammonia recovery unit 384 via stream 396. The amines rich stream from ammonia recovery unit 384 is sent to the water removal system 316 via stream 338. Water can be removed from the amines rich stream preferably via conventional distillation. The water is sent overhead to the wastewater treatment system 318 via stream 342 and the amines are sent to the product refining system 320 via stream 340 (preferably conventional distillation using dividing wall columns). As shown, product refining system 320 separates the amines into eight products: monoethanolamine product 350, diethanolamine product 352, triethanolamine product 354, ethylenediamine product 356, piperazine product 358, diethylenetriamine product 360, amine heavies 362, and aminoethylethanolamine product 364. Optionally, it may be deemed that aminoethylethanolamine may not exist in quantities sufficient enough to warrant investment for recovery and thus will be recovered with amine heavies 362. To the extent any alkylethyleneamines are present in stream 338, said alkylethyleneamines can be removed with the water in system 316 via the azeotropic method described above in connection with FIG. 4 and sent to wastewater treatment system 318 or said alkylethyleneamines can be sent to the product refining system 320. For example, if alkylethylenediamines are sent to product refining system 320, said alkylethylenediamines typically end up in the ethylenediamine product 356. Optionally, at least a portion of monoethanolamine separated in refining system 320 can be recycled and introduced into reactor 308 via stream 344.

EXAMPLES

Catalyst Preparation

The catalyst used in Examples 1 and 2 below was prepared as described below. Precursor salts of the Nickel (Ni), Rhenium (Re), and Boron (B) were dissolved in 70-80° C. water to form an impregnation solution. The final volume of the impregnation solution was adjusted to equal the adsorption volume required for the number of times that the carrier was impregnated, and the quantities of the precursor salts were those calculated to give the metal compositions provided in the examples. In each case the carrier was impregnated to incipient wetness by the addition of the appropriate amount of impregnation solution and gently agitated until all the liquid was adsorbed. The sample was then placed in a muffle furnace and calcined in air for one hour at 340° C. When the support had cooled, additional impregnations were performed until all of the solution had been added. A calcination step at 340° C. was done after each impregnation. Prior to use, the catalyst compositions were reduced in hydrogen by ramping the temperature at 3° C./min to 230° C., holding at 230° C. for one hour, and then ramping at 3° C./min to 340° C., and holding for 3 hours. The catalyst compositions were allowed to cool under hydrogen to ambient temperature, after which they were stabilized by adding a flowing stream of 1% oxygen in nitrogen gas until the exotherm ceased. At no time was the exotherm allowed to exceed about 70° C.

Example 1

Example 1 shows the product mix from a reductive amination process where the effluent from the reaction between ethylene oxide and ammonia is fed to the reductive amination reactor. Such effluent includes MEA, DEA, TEA, and ammonia. Accordingly, Example 1 is indicative of the product mix coming out of the reductive amination reactor in FIG. 1, described above.

The reductive amination reaction in Example 1 was conducted over 125 grams of a Ni—Re—B catalyst prepared as described above. The feed consisted of liquid consisting of 17.9 wt % Water, 59.3 wt % Monoethanolamine, 17.1 wt % Diethanolamine, and 5.7 wt % Triethanolamine. Sufficient Ammonia to yield an Ammonia to Monoethanolamine mole ratio of 18.9 was added, along with 1.4 mol % Hydrogen (on a total feed basis). Reaction was conducted at a temperature of 165° C. and a pressure of 3018 psia, 924 grams per hour total feed. The reaction product was analyzed via capillary gas chromatography. Monoethanolamine conversion was 23.3%, Diethanolamine conversion was 12.1%. Selectivity on a dry weight basis (i.e., on a reactant-free and water-free basis) was 74.2% by weight to Ethylenediamine, 1.7% by weight to piperazine, 2.3% by weight to Diethylenetriamine, 14.0% by weight to aminoethylethanolamine, and 7.8% by weight to various heavies.

In a fully integrated ethanolamine-ethyleneamine process such as illustrated in Example 1, a lower monoethanolamine conversion is possible, since the entire monoethanolamine output from the ethoxylation reactor is not normally devoted to making ethyleneamines.

Example 2

Example 2 shows the product mix from a reductive amination process where MEA and ammonia are fed to the reductive amination reactor. Accordingly, Example 2 is indicative of the product mix coming out of the reductive amination reactors in FIG. 2 or 3, described above.

The reductive amination reaction for Example 2 took place over a Nickel/Rhenium/Boron (8.0:2.0:1.7 wt. percent) catalyst on an alumina/silica (80:20) support prepared as described above. The catalyst was loaded into 86.25" of 0.688" ID tubular stainless steel adiabatic reactor. MEA and ammonia were fed into a mixer to provide an ammonia/MEA molar feed ratio of approximately 10. Hydrogen was also fed to yield a feed mix that was 1-2 mol % hydrogen. The mixture was fed to a reactor preheated to 165° C. at a pressure of 3000 psig and a space velocity of 10-12 g-mol MEA/kg catalyst/hour. The liquid sample was collected in a receiver at ambient temperature, to allow the ammonia and hydrogen to flash off. The product mix of reaction at 37.5% MEA conversion was as, follows: is 88.2% by weight EDA, 2.2% by weight PIP, 5.4% by weight DETA, 3.3% by weight AEEA, and 0.9% by weight Others. The product mix was determined by capillary gas chromatography on a dry product basis (i.e., on a reactant-free and water-free basis).

Example 3

Example 3 illustrates how alkylethylenediamines can be separated from ethylenediamine (EDA) via the azeotropic method explained above with respect to FIG. 4. A stream containing 0.115% by weight N-Ethylethylenediamine (EtEDA), 0.189% by weight N-Methylethylenediamine (MeEDA), 18.446% by weight ethylenediamine (EDA) 11.965% by weight Water and 69.285% of other ethanolamines and ethyleneamines (stream 402 in system 400) is fed to a water column (402). The water column contains 72 trays (numbered bottom to top with the bottom or lowest tray numbered 1) and the water column feed is introduced at tray 59. With the water column operating at head pressure of 23.7 psia, a head temperature of 115 C and a base temperature 176C, the composition of the overhead water make from a total condenser is 97.46% Water, 0.19% EtEDA 1.48% Me EDA and 0.16% EDA. At the conditions in the base of the water column, the bottoms stream 406 from the water column 404 will contain 1.5% water. Stream 406 is then feed into an EDA column 408 containing 46 trays (numbered bottom to top with the bottom or lowest tray numbered 1) with the feed going to tray 13. The EDA Column runs with a head pressure of 140 mmHg with a head temperature of 66 C and a base temperature of 144 C. EDA product Stream 410 is removed overhead in column 408 and has a composition of 0.027% by weight EtEDA, 0.043% by weight MeEDA, 99.861% by weight EDA 0.066% by weight Water and 0.004% of other ethanolamines and ethyleneamines. The water contained in stream 406 entering column 408 is removed from a side draw 412 on tray 18 and returned to tray 30 of water column 404.

The resultant EDA product 410 contains 700 parts per million by weight alkylethylenediamine. Without this invention, the alkylethylenediamine content in the EDA product would be 16,000 parts per million by weight alkylethylenediamine making the EDA material unacceptable for many applications Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention.

What is claimed is:

1. A process for the manufacture of one or more ethanolamines and one or more ethyleneamines comprising the steps of:
   a) combining ethylene oxide with ammonia;
   b) a first reacting step comprising reacting ethylene oxide with ammonia in a manner to produce one or more ethanolamines, wherein said first reacting step forms a first effluent comprising:
      i) unreacted ammonia; and
      ii) the one or more ethanolamines;
   c) a second reacting step comprising reacting at least a portion of the first effluent in the presence of a reductive amination catalyst to produce one or more ethyleneamines, wherein said second reacting step forms a second effluent comprising:
      i) unreacted ammonia;
      ii) one or more alkylamines, wherein the one or more alkylamines are chosen from methylamine, ethylamine, and combinations thereof;
      iii) one or more unreacted ethanolamines; and
      iv) the one or more ethyleneamines;
   d) separating the unreacted ammonia and one or more alkylamines from the second effluent;
   e) separating the unreacted ammonia from the one or more alkylamines; and
   f) after separating the unreacted ammonia from the one or more alkylamines, recycling the unreacted ammonia so as to be combined with the ethylene oxide in the step of combining ethylene oxide with ammonia.

2. The process of claim 1, wherein the second reacting step comprises reacting all of the first effluent in the presence of a reductive amination catalyst to produce one or more ethyleneamines.

3. The process of claim 1, further comprising the step of, after the step of separating the unreacted ammonia and one or more alkylamines from the second effluent, removing water from the second effluent.

4. The process of claim 1, wherein the one or more ethanolamines are selected from the group consisting of: monoethanolamine, diethanolamine, triethanolamine, and combinations thereof, and wherein the one or more ethyleneamines are selected from the group consisting of: ethylenediamine, diethylenetriamine, triethylenetetramine, tetraethylenepentamine, piperazine, aminoethylpiperazine, aminoethylethanolamine, heavy polyamine, and combinations thereof.

5. The process of claim 1, wherein the ammonia in the step of reacting ethylene oxide with ammonia is anhydrous ammonia.

6. The process of claim 1, wherein the ammonia in the step of reacting ethylene oxide with ammonia is in solution with water, wherein the water is present in an amount of five percent by weight of ammonia and water or less.

7. The process of claim 1, wherein after the step of separating the unreacted ammonia from the one or more alkylamines, the amount of alkylamines present in the stream of unreacted ammonia is less than 100 parts per million by weight.

8. The process of claim 1, wherein after the step of separating the unreacted ammonia from the one or more alkylamines, the amount of alkylamines present in the stream of unreacted ammonia is less than 50 parts per million by weight.

9. A process for the manufacture of one or more ethanolamines and one or more ethyleneamines comprising the steps of:
   a) combining ethylene oxide with ammonia;
   b) a first reacting step comprising reacting ethylene oxide with ammonia in a manner to produce one or more ethanolamines, wherein said first reacting step forms a first effluent comprising:
      i) unreacted ammonia; and
      ii) the one or more ethanolamines;
   c) separating at least a portion of the unreacted ammonia from the first effluent;
   d) after separating the at least a portion of the unreacted ammonia from the first effluent, recycling the unreacted ammonia so as to be combined with the ethylene oxide in the step of combining ethylene oxide with ammonia;
   e) a second reacting step comprising reacting one or more ethanolamines made in the first reacting step and ammonia in the presence of a reductive amination catalyst to produce one or more ethyleneamines, wherein said second reacting step forms a second effluent comprising:

i) unreacted ammonia;
    ii) one or more alkylamines, wherein the one or more alkylamines are chosen from methylamine, ethylamine, and combinations thereof;
    iii) one or more unreacted ethanolamines; and
    iv) the one or more ethyleneamines;
  f) separating at least a portion of the unreacted ammonia and at least a portion of the one or more alkylamines from the second effluent; and
  g) after separating the unreacted ammonia and at least a portion of the one or more alkylamines from the second effluent, recycling the unreacted ammonia and the at least a portion of the one or more alkylamines so as to be combined with the one or more ethanolamines and ammonia in the second reacting step.

10. The process of claim 9, wherein the one or more ethanolamines comprise at least monoethanolamine.

11. The process of claim 9, wherein the one or more ethanolamines consist essentially of mono ethanolamine.

12. The process of claim 9, further comprising the steps of:
  a) after separating the at least a portion of the unreacted ammonia from the first effluent and after separating the unreacted ammonia and at least a portion of the one or more alkylamines from the second effluent, combining the first and second effluents to form a third effluent;
  b) separating unreacted ammonia from the third effluent; and
  c) after separating unreacted ammonia from the third effluent, recycling the unreacted ammonia in a manner so as to be combined with the ammonia in the second reacting step.

13. The process of claim 12, further comprising the step of, after the unreacted ammonia is separated from the third effluent, removing water from the third effluent.

14. The process of claim 13, further comprising the steps of, after the water is removed from the third effluent:
  a) separating the one or more ethanolamines and one or more ethyleneamines from the third effluent into individual components; and
  b) recycling at least a portion of the monoethanolamine so as to combine the monoethanolamine with ammonia in the step of reacting the monoethanolamine with at least a portion of the unreacted ammonia in the presence of a reductive amination catalyst to produce one or more ethyleneamines.

15. A process for the manufacture of one or more ethanolamines and one or more ethyleneamines comprising the steps of:
  a) combining ethylene oxide with ammonia;
  b) a first reacting step comprising reacting ethylene oxide with ammonia in a manner to produce one or more ethanolamines, wherein said first reacting step forms a first effluent comprising:
    i) unreacted ammonia; and
    ii) the one or more ethanolamines;
  c) separating at least a portion of the unreacted ammonia from the first effluent so as to form a second effluent;
  d) after separating the at least a portion of the unreacted ammonia from the first effl$_{uent}$, recycling the unreacted ammonia so as to be combined with the ethylene oxide in the step of combining ethylene oxide with ammonia;
  e) a second reacting step comprising reacting at least a portion of the second effluent in the presence of a reductive amination catalyst to produce one or more ethyleneamines, wherein said second reacting step forms a third effluent comprising:
    i) unreacted ammonia;
    ii) one or more alkylamines, wherein the one or more alkylamines are chosen from methylamine, ethylamine, and combinations thereof;
    iii) one or more unreacted ethanolamines; and
    iv) the one or more ethyleneamines
  f) separating the unreacted ammonia and at least a portion of the one or more alkylamines from the third effluent;
  g) after separating the unreacted ammonia and at least a portion of the one or more alkylamines from the third effluent, recycling the unreacted ammonia and the at least a portion of the one or more alkylamines so as to be combined with the second effluent.

16. The process of claim 15, wherein the second effluent in the second reacting step comprises one or more ethanolamines comprising at least monoethanolamine.

17. The process of claim 15, wherein the second effluent in the second reacting step comprises an ethanolamine consisting essentially of monoethanolamine.

18. The process of claim 15, wherein the step of separating at least a portion of the unreacted ammonia from the first effluent comprises separating the first effluent into at least three compositions comprising:
  a) a first composition comprising the at least a portion of the unreacted ammonia, wherein said unreacted ammonia is recycled so as to be combined with the ethylene oxide in the step of combining ethylene oxide with ammonia;
  b) a second composition comprising at least a portion of the unreacted ammonia and monoethanolamine, wherein said monoethanolamine and ammonia are reacted in the presence of a reductive amination catalyst to produce one or more ethyleneamines; and
  c) a third composition comprising monoethanolamine, diethanolamine, and triethanolamine.

19. The process of claim 18, wherein the step of separating the first effluent into at least three compositions comprises introducing the first effluent into an inter-reactor separator in a manner so as to form the at least three compositions.

* * * * *

UNITED STATES PATENT AND TRADEMARK OFFICE
CERTIFICATE OF CORRECTION

PATENT NO.        : 8,383,861 B2                                    Page 1 of 1
APPLICATION NO.   : 12/587358
DATED             : February 26, 2013
INVENTOR(S)       : David Do et al.

It is certified that error appears in the above-identified patent and that said Letters Patent is hereby corrected as shown below:

In the Claims:

Column 26
Line 6, "effl$_{uent'}$" should be -- effluent --

Signed and Sealed this
Twenty-eighth Day of May, 2013

Teresa Stanek Rea
*Acting Director of the United States Patent and Trademark Office*